United States Patent [19]

Soo et al.

[11] Patent Number: 4,967,018
[45] Date of Patent: Oct. 30, 1990

[54] MONOALKYLENE GLYCOL PRODUCTION USING MIXED METAL FRAMEWORK COMPOSITIONS

[75] Inventors: Hwaili Soo; Bernard C. Ream; John H. Robson, all of Charleston

[73] Assignee: Union Carbide Chemicals and Plastics Company Inc., Danbury, Conn.

[21] Appl. No.: 423,703

[22] Filed: Oct. 18, 1989

Related U.S. Application Data

[63] Continuation of Ser. No. 125,134, Nov. 25, 1987, abandoned.

[51] Int. Cl.$^5$ ............... C07C 29/00; C07C 31.20; C07C 33/26; C07C 35/11
[52] U.S. Cl. ............................ 568/867; 568/811; 568/833; 568/857
[58] Field of Search ............. 568/867, 833, 811, 857

[56] References Cited

U.S. PATENT DOCUMENTS

| | | | |
|---|---|---|---|
| 4,014,945 | 3/1977 | Zimmerscheid et al. | 568/867 |
| 4,233,221 | 11/1980 | Raines et al. | |
| 4,277,632 | 7/1981 | Kumazawa et al. | 568/867 |
| 4,476,324 | 10/1984 | Reichle | 568/389 |
| 4,551,566 | 11/1985 | Robson et al. | 568/811 |
| 4,578,524 | 3/1986 | Keen | 568/811 |
| 4,701,571 | 10/1987 | Soo et al. | 568/867 |
| 4,760,200 | 7/1988 | Keen et al. | 568/867 |
| 4,774,212 | 9/1988 | Drezdon | 502/62 |
| 4,843,168 | 6/1989 | Drezdzon et al. | 558/357 |

OTHER PUBLICATIONS

Itaya, et al., *Inorg. Chem.*, vol. 26, pp. 624–626, 1987.
Chem Abstracts, vol. 95, Entry 97099m, Alkylene glycol ether acetates, (japanese Kokai No. 81/36,431).
Chem Abstracts, vol. 93, Entry 49705t, Water-reisistant magnesium hydroxide or hydrotalcite-analog pellets, (Jap. Kokai No. 80/28750).
Reichle, et al., "Anionic Clay Minerals", *Chemtech*, 1/86, pp. 58–63.
Bish, *Bull. Mineral.*, vol. 103, pp. 170–175, 1980.
Miyata, et al., *Clays and Clay Minerals*, vol. 26, pp. 441–447, 1978.
Brindley, et al., *Clays and Clay Minerals*, vol. 28, pp. 87–91, 1980.
Miyata, et al., *Clays and Clay Minerals*, vol. 25, pp. 14–18, 1977.
Brindley, et al., *American Mineralogist*, vol. 64, pp. 836–843, 1979.
Sasaki, et al., *Journal of Physical Chemistry*, vol. 88, pp. 1716–1719, 1984 (Abstract only).
Miyata, *Clays and Clay Minerals*, vol. 31, pp. 305–311, 1983 (Abstract only).
Giannelis, et al., *Inorg. Chem.*, vol. 26, pp. 203–205, 1987.
Japanese Kokai 81/36431, published 4/9/81 (Abstract only).
Japanese Kokai 80/28750, published 2/29/80 (Abstract only).
Hamilton, et al., *Industrial and Engineering Chemistry*, vol. 49, pp. 838–846 (1987).
Reichle, Manuscript entitled "Catalytic Reactions by Thermally Activated, Synthetic Anionic Clay Materials".
Japanese Kokai No. 58/159849 (1983).
Taylor, R. M., *Clay Minerals* (1984), 19:591–603.
Japanese Kokai No. 48/22406.
Japanese Kokai No. 55/69525.
Japanese Kokai No. 57/106631.
Japanese Kokai No. 58/150435.

Primary Examiner—J. E. Evans
Attorney, Agent, or Firm—Norman L. Balmer

[57] ABSTRACT

A process for the catalytic hydrolysis of alkylene oxide to alkylene glycol using a hydrothermally stable, mixed metal framework catalyst composition selected from
(a) material having the formula

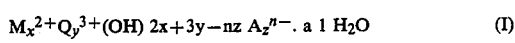

$$M_x{}^{2+}Q_y{}^{3+}(OH)_{2x+3y-nz} A_z{}^{n-} \cdot a \, 1 \, H_2O \quad (I)$$

wherein M is at least one divalent metal cation; Q is at least one trivalent metal cation; and A is at least one anion providing a valence ($n^{31}$), wherein n is at least 1, and wherein a is a positive number, M, Q, and A are provided in a proportion such that x/y is a number equal to or greater than 1, z has a value greater than zero and 2x+3y−nz is a positive number, and M, Q and A are selected to provide a layered structure, and
(b) material prepared by calcining the material of formula (I) having the formula

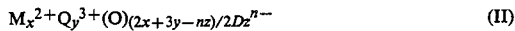

$$M_x{}^{2+}Q_y{}^{3+}(O)_{(2x+3y-nz)/2}D_z{}^{n-} \quad (II)$$

wherein M, Q, x, y, z and n have the same meanings defined above in connection with formula (I) and D is at least one nonvolatile anion.

16 Claims, No Drawings

MONOALKYLENE GLYCOL PRODUCTION USING MIXED METAL FRAMEWORK COMPOSITIONS

This application is a continuation of prior U.S. application Ser. No. 125,134, filing date Nov. 25, 1987, now abandoned.

BACKGROUND OF THE INVENTION

1. Field of the Invention

This invention relates to the production of alkylene glycols by heterogeneous catalysis from alkylene oxides and water using hydrothermally stable catalysts. The invention also relates to a new class of hydrothermally stable mixed metal framework compositions. The new compositions are useful as catalysts for preparing alkylene glycols from alkylene oxides using either liquid or vapor phase hydrolysis.

2. Description of Related Art

Commercial processes for preparing alkylene glycols, for example, ethylene glycol, propylene glycol and butylene glycol, involve liquid-phase hydration of the corresponding alkylene oxide in the presence of a large molar excess of water (see, for example, Kirk-Othmer, *Encyclopedia of Chemical Technology*, Vol. 11, Third Edition, page 939 (1980)). The hydrolysis reaction typically is conducted at moderate temperatures, e.g., from about 100° C. to about 200° C., and elevated pressures with water typically being provided to the reaction zone in excess of 15 moles per mole of alkylene oxide. The primary by-products of the hydrolysis reaction include di- and polyglycols, e.g., dialkylene glycol, trialkylene glycol and tetra-alkylene glycol. The di- and polyglycols are believed to be formed primarily by reaction of alkylene oxide with alkylene glycol, as alkylene oxides are generally more reactive with alkylene glycols than they are with water. The large excess of water is employed in order to favor the reaction with water instead and thereby obtain a commercially-attractive selectivity to the monoglycol product.

Due to the large excess of water, recovery of alkylene glycol from the hydrolysis reaction mixture is very energy intensive. Typically, water is removed by evaporation to leave an alkylene glycol-containing residue which is purified further by distillation. A process which would permit a reduction in the amount of water employed while maintaining, or enhancing selectivity toward the monoglycol product would be highly desirable.

While the hydrolysis reaction can proceed uncatalyzed, the presence of acids or bases enhances the rate of reaction. Acid and base catalysts do have shortcomings, however. For instance, base catalysts generally do not beneficially affect selectivity to the formation of the monoglycol product and the use of acid catalysts typically is accompanied by corrosion problems. Hence, commercial processes typically utilize relatively neutral hydrolysis conditions (for instance, pH 6-10).

Representative of the numerous acid catalysts that have been suggested for use in hydration of alkylene oxides include fluorinated alkyl sulfonic acid ion exchange resins (U.S. Pat. No. 4,165,440, issued Aug. 21, 1979); carboxylic acids and halogen acids (U.S. Pat. No. 4,112,054, issued Sept. 5, 1978); strong acid cation exchange resins (U.S. Pat. No. 4,107,221, issued Aug. 15, 1978); aliphatic mono- and/or polycarboxylic acids (U.S. Pat. No. 3,933,923, issued Jan. 20, 1976); cationic exchange resins (U.S. Pat. No. 3,062,889, issued Nov. 6, 1962); acidic zeolites (U.S. Pat. No. 3,028,434, issued Apr. 3, 1962); sulfur dioxide (U.S. Pat. No. 2,807,651, issued Sept. 24, 1957); trihalogen acetic acids (U.S. Pat. No. 2,472,417, issued June 7, 1949); and copper-promoted aluminum phosphate (U.S. Pat. No. 4,014,945, issued Mar. 29, 1977).

In addition to the acid catalysts, numerous other catalysts have been suggested for the hydration of alkylene oxides in the presence of carbon dioxide. These include alkali metal halides, such as chlorides, bromides and iodides; quaternary ammonium halides such as tetramethyl ammonium iodide and tetramethyl ammonium bromide (British Pat. No. 1,177,877); organic tertiary amines such as triethylamine and pyridine (German patent application Ser. No. 2,615,595, Oct. 14, 1976, and U.S. Pat. No. 4,307,256, issued Dec. 22, 1981); quaternary phosphonium salts (U.S. Pat. No. 4,160,116, issued July 3, 1979); chlorine or iodine-type anion exchange resins (Japanese Kokai No. 57/139,026, published Aug. 27, 1982); and partially amine-neutralized sulfonic acid catalyst, e.g., partially amine-neutralized sulfonic acid resin (U.S. Pat. No. 4,393,254, issued July 12, 1983).

Various metal-containing compounds, including metal oxides, also have been proposed as catalysts for the hydrolysis of alkylene oxides. For example, U.S. Pat. No. 2,141,443, issued Dec. 27, 1938, discloses the production of glycols by reacting alkylene oxide with water in the presence of a dehydrating metal oxide, for example, alumina, thoria, or oxides of tungsten, titanium, vanadium, molybdenum or zirconium. The reaction is carried out in the liquid phase and under conditions of temperature and pressure suited to maintain such phase. In example 7, the patentees disclose rendering a yellow tungstic acid catalyst more mechanically stable by admixture with a mixture of silicon ester, alcohol and water, followed by drying the catalyst. Similarly, U.S. Pat. No. 2,807,651, issued Sept. 24, 1957, states that it is known to catalyze the reaction of alkylene oxide and water using alkali metal bases, alcoholates, and oxides of titanium, tungsten and thorium.

Many metals such as vanadium, molybdenum, tungsten, titantium, chromium, zirconium, selenium, tellurium, tantalum, rhenium, uranium and niobium, also have been proposed as components for catalysts for preparing 1,2-epoxides of alpha-olefins and organic hydroperoxides and often are present during a subsequent hydrolysis reaction. For instance, Examples I and III of U.S. Pat. No. 3,475,499, issued Oct. 28, 1969, disclose that a mixture of normal alpha-olefins containing 11 to 15 carbon atoms was epoxidized with ethylbenzene hydroperoxide in the presence of molybdenum naphthenate catalyst. After distillation, the bottoms, which contained the 1,2-epoxides and the molybdenum-containing catalyst, were contacted with water containing 0.5 percent sodium hydroxide at a temperature of 90° C. That reaction product was distilled and a conversion of 1,2-epoxides was reported to be 100 percent and the selectivity to 1,2-glycols was reported to be 94 percent.

More recently, U.S. Pat. No. 4,277,632, issued July 7, 1981, discloses a process for producing alkylene glycol by hydrolysis of alkylene oxide in the presence of a catalyst of at least one member selected from the group consisting of molybdenum and tungsten. The catalyst may be metallic molybdenum or metallic tungsten, or inorganic or organic compounds thereof, such as oxides, acids, halides, phosphorous compounds, polyacids, alkali metal and alkaline earth metal, ammonium salts and heavy metal salts of acids and polyacids, and organic acid salts. An objective of the disclosed process is stated to be the hydrolysis of alkylene oxides wherein water is present in about one to five times the stoichiometric value without forming appreciable amounts of by-products such as the polyglycols. The reaction may be carried out in the presence of carbon dioxide. When the reaction is carried out in the presence of nitrogen, air, etc., the patentees state that the pH of the reaction mixture should be adjusted to a value in the range of 5 to 10. Japanese Kokai No. JA 54/128,507, published Oct. 5, 1979, discloses a process for producing alkylene glycols from alkylene oxides and water using metallic tungsten and/or tungsten compounds.

Japanese Kokai No. 56/073,035, published June 17, 1981, discloses a process for the hydrolysis of alkylene oxide in the presence of a carbon dioxide and a catalyst consisting of a compound containing at least one element selected from the group of titanium, zirconium, vanadium, niobium, tantalum and chromium. The compounds include the oxides, sulfides, acids, halides, phosphorous compounds, polyacids, alkali metal salts of acids and polyacids, ammonium salts of acids and polyacids, and heavy metal salts of acids.

Japanese Kokai No. 56/073,036, published June 17, 1981, discloses a process for the hydrolysis of alkylene oxide in the presence of a carbon dioxide atmosphere and a catalyst consisting of a compound containing at least one element selected from a group comprising aluminum, silicon, germanium, tin, lead, iron, cobalt and nickel.

Japanese Kokai No. 56/92228, published July 25, 1981, is directed to processes for producing highly pure alkylene glycols. The disclosure is directed to a distillation procedure for recovering a molybdenum and/or tungsten-containing catalyst from an alkylene oxide hydrolysis product in the presence of carbon dioxide. The application states that the catalyst is at least one compound selected from the group consisting of compounds of molybdenum and tungsten which compound may be in combination with at least one additive selected from the group consisting of compounds of alkali metals, compounds of alkaline earth metals, quaternary ammonium salts and quaternary phosphonium salts. The preferred catalysts are stated to be molybdic acid, sodium molybdate, potassium molybdate, tungstic acid, sodium tungstate and potassium tungstate. Potassium iodide is the only additive employed in the examples. For a similar disclosure see also Japanese Kokai No. 56/90029.

U.S. Pat. No. 4,551,566—J. H. Robson and G. E. Keller, discloses producing monoalkylene glycols with high selectivity by reacting a vicinal alkylene oxide with water in the presence of a water-soluble vanadate. Lower water to alkylene oxide ratios can be employed using the disclosed process with attractive selectivities to monoglycol products. The counter ion to the vanadate is selected to provide a water-soluble vanadate salt under the reaction conditions employed and alkali metals, alkaline earth metals, quaternary ammonium, ammonium, copper, zinc, and iron are suggested cations. It also is disclosed that the vanadate may be introduced into the reaction system in the salt form or on a support such as silica, alumina, zeolites and clay. Since the vanadate ion is water-soluble, it can be lost from the reaction system and means must be provided to recover it from the effluent from the reaction zone. In U.S. Pat. No. 4,578,524, the reaction of alkylene oxide and water to form monoalkylene glycol is carried out in the presence of a dissociatable vanadate salt and carbon dioxide.

Unfortunately, insoluble salts of metavanadate, such as calcium metavanadate, as well as insoluble molybdate, tungstate, etc., and other metalate salts do not appear to provide the selectivity enhancement toward the monoglycol products which is achievable with the water-soluble salts. Hence, problems with the recovery of the water-soluble salts are significant factors in considering the use of the technology on a commercial scale.

U.S. Pat. No. 4,667,045—J. R. Briggs and J. H. Robson discloses producing alkylene glycols with high selectivity from alkylene oxides and water, either as a liquid or vapor, in the presence of organosalts of a metalate anion having at least one cyclic alkylenedioxy moiety. Particularly preferred metals for the metalate anions are vanadium, molybdenum and tungsten.

European Patent Publication 160,330 describes a process for making alkylene glycols from alkylene oxide and water in the presence of a metalate anion which is associated with an electropositive complexing site on a solid support, such as an anion exchange resin. Again, metalate anions of the metals vanadium, molybdenum and tungsten are preferred.

Japanese Kokai No. 48/22406 discloses using calcium apatite as either a liquid or vapor phase hydrolysis catalyst for making alkylene glycol from alkylene oxide, such as ethylene oxide.

Japanese Kokai No. 55/69525 and Japanese Kokai No. 57/106631 disclose using hydrotalcite ($Mg_6Al_2(OH)_{16}CO_3.4H_2O$) and its analogs where magnesium is replaced by calcium, zinc, copper or nickel; aluminum is replaced by iron or chromium, and carbonate is replaced by chloride, bromide, fluoride, nitrate, acetate, cyanate, sulfate, chromate, oxalate, phosphate or ferrocyanate, with the stoichiometry adjusted appropriately, as a catalyst for preparing ethylene glycol by reacting ethylene carbonate and water. The disclosures note that these hydrotalcite-type catalysts are easily separated from the liquid reaction medium and are stable under the hydrolysis reaction conditions (130° C.-160° C.). Other catalysts for hydrolyzing alkylene carbonates also are disclosed in Japanese Kokai No. 58/150435 (a zinc compound supported on an alumina or silica-alumina carrier) and Japanese Kokai No. 58/159849 (a copper compound supported on an alumina or silica-alumina carrier).

DESCRIPTION OF THE INVENTION

One aspect of the present invention broadly relates to processes for producing monoalkylene glycols by reacting water supplied as either a liquid or vapor with vicinal alkylene oxide in the presence of a hydrothermally stable, mixed metal framework catalyst composition. In a first aspect, the mixed metal framework composition comprises material having the formula:

$$M_x^{2+}Q_y^{3+}(OH)_{2x+3y-nz}A_z^{n-}.aH_2O \qquad (I)$$

wherein M is at least one divalent metal cation; Q is at least one trivalent metal cation; and A is at least one anion providing a valence ($n^-$), wherein n is at least 1, e.g., between 1 and 4 and most often between 1 and 3, and wherein a is a positive number, M, Q, and A are provided in a proportion such that x/y is a number equal to or greater than 1, z has a value greater than zero and $2x+3y-nz$ is a positive number, and M, Q and A are selected to provide a layered structure. Preferably, x/y is in the range of 1 to 12, more preferably x/y is in the range of 1 to 6 and most preferably is in the range of 1 to 4. Preferably, z has a value such that x/z is between n and 12n, more preferably between n and 6n and most preferably between n and 4n.

Suitable divalent metal cations, M, broadly include elements selected from the Transition elements and Groups IIA, IVA and VA of the Periodic Table as well as certain rare earth elements. As specific examples can be mentioned magnesium, calcium, titanium, vanadium, chromium, manganese, iron, cobalt, nickel, palladium, platinum, copper, zinc, cadmium, mercury, tin and lead. Divalent metal cations which are particularly suitable are magnesium, nickel, cobalt, zinc, calcium, iron and copper. Suitable trivalent metal cations, Q, broadly include elements selected from the Transition elements and Groups IIIA and VA of the Periodic Table as well as certain rare earth elements and Actinide elements. As specific examples can be mentioned aluminum, antimony, titanium, scandium, bismuth, vanadium, yttrium, chromium, iron, manganese, cobalt, ruthenium, nickel, gold, gallium, thallium, and cerium. Trivalent metal cations which are particularly suitable can be selected from aluminum, iron and chromium.

The composition of formula (I) also can include a wide range of anions, A. Any anion or combination of anions which can balance the charge of the cations without significantly disrupting the layered structure of the mixed metal framework composition can be used. Suitable anions include inter alia, halides, (such as chloride, fluoride, bromide, and iodide), nitrite, nitrate, sulfite, sulfate, sulfonate, carbonate, chromate, cyanate, phosphite, phosphate, molybdocyanate, bicarbonate, hydroxide, arsenate, chlorate, ferrocyanide, borate, cyanide, cyanaurate, cyanaurite, ferricyanide, selenate, tellurate, bisulfate, as well as organic anions such as oxalate, acetate, hexanoate, sebacate, formate, benzoate, malonate, lactate, oleate, salicylate, stearate, citrate, tartrate, maleate, and the like. The class of metalate anions described in Briggs et al. U.S. Pat. No. 4,667,045, the disclosure of which is incorporated herein by reference, including metavanadate, orthovanadate, molybdate, tungstate, hydrogen pyrovanadate and pyrovanadate, also are suitable as anion A. Anions suitable for use in combination with the metal cations previously identified as being particularly suitable are carbonate, halide, cyanide, phosphate, chromate, sulfate, oxalate, acetate, nitrate, hexanoate, sebacate, vanadate, molybdate, tungstate and ferrocyanate.

The moieties representing M, Q and A are selected to provide the desired layered structure in the mixed metal framework composition. While not wishing to be limited by theory, it is believed that the cation moieties and anion moieties for a particular mixed metal framework composition generally should have similar sizes in order to provide the layered structure. For instance, the anion(s) A typically locate between spaced layers of the mixed metal lattice. If two anions (A) are of substantially different sizes, significant disruptions of the layered structure could occur.

The foregoing lists of suitable divalent and trivalent cations and suitable anions are meant to be illustrative and not exclusive. Those skilled in the art will recognize that other cations and anions can be used provided that the specific type of cations and their relative amounts (x/y ratio) and the specific type of anions and their relative amount result in a mixed metal framework composition of the desired layered structure.

A particularly interesting subset of the materials identified above are based on exchangeable anionic clay minerals. For example, compositions of formula (I) wherein M is magnesium and Q is aluminum are related to hydrotalcites, while compositions in which M is nickel and A is aluminum are related to takovites. In fact, catalysts prepared using magnesium, nickel or cobalt as the divalent cation and aluminum as the trivalent cation exhibit the typical X-ray diffraction pattern of hydrotalcite with a wide variety of anions. While the compositions broadly embraced by formula (I) will be referred to throughout the application as mixed metal framework materials, the particular subclasses of materials based on magnesium or nickel and aluminum simply will be referred to as hydrotalcite-type materials.

In another aspect, the present invention also relates to the catalytic production of monoalkylene glycols from vicinal alkylene oxide and water supplied as either a liquid or vapor in the presence of hydrothermally stable mixed metal framework compositions prepared by calcining at an elevated temperature compositions according to formula (I). The composition can be calcined either at a condition where the layered structure of the pre-calcined material can be restored, or at a condition which irreversibly destroys such layered structure. Suitable calcined compositions have the general formula:

$$M_x^{2+}Q_y^{3+}(O)_{(2x+3y-nz)/2} D_z^{n-} \qquad (II)$$

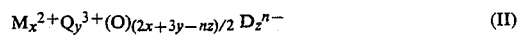

wherein M, Q, x, y, z and n have the same meanings defined above in connection with formula (I), and D is at least one nonvolatile anion. Nonvolatile anions may include, inter alia, halides, phosphites, phosphate, vanadate, molybdate, tungstate, sulfite, sulfate, chromate, arsenate, borate, chlorate and the like. This list is illustrative and not exclusive.

Heat treating the formula (I) compositions to prepare the calcined mixed metal framework compositions of formula (II) can be done, for example, at a temperature in the range of 400° C. to 600° C. for a period of time of about 12 to 24 hours under an inert atmosphere such as nitrogen or in appropriate cases under an oxidizing atmosphere such as air.

Calcination of the metal framework compositions of the present invention dehydrates the composition, converts the metal hydroxides to metal oxides and transforms the layered or plate-like structure of the metal lattice basically into a structure of metal oxides. Also, any nonvolatile anions in the calcined material no longer have the attributes of a dissociated ion, as they may have had in the uncalcined composition.

Provided the calcination temperature is not excessive, the layered structure of the hydrated mixed metal framework composition can be restored or regenerated simply by rehydration of the calcined material with water. Generally, the layered structure can be restored readily if the calcination temperature does not exceed about 600° C. Calcined compositions which can be rehydrated in this fashion will be referred to as reversibly calcined materials. The layered structure of mixed metal framework compositions calcined under more severe conditions, e.g., at more severe temperatures, however, cannot be regenerated and will be referred to as irreversibly calcined materials. Within the broad practice of the present invention both reversibly and irreversibly calcined materials can be used to catalyze the preparation of monoalkylene glycols from vicinal alkylene oxide and water. Thus, as used throughout the specification and claims, the phrase "mixed metal framework composition" and the like is intended to include both the hydrated mixed metal compositions of formula (I) which exhibit a layered structure, as described above, and the calcined products thereof of formula (II).

Another aspect of the present invention relates to new hydrothermally stable, mixed metal framework compositions which are particularly suitable as catalysts for preparing monoalkylene glycol at high selectivity from alkylene oxide and water in the liquid phase. On the one hand, these new mixed metal framework compositions comprise materials having the formula:

$$M_x^{2+}Q_y^{3+}(OH)_{2x+3y-nz}E_z^{n-}\cdot aH_2O \quad (III)$$

wherein M is at least one divalent metal cation; Q is at least one trivalent metal cation; E is at least one anion selected from metavanadate, orthovanadate, hydrogen pyrovanadate, pyrovanadate, molybdate and tungstate and wherein a is a positive number, M, Q and E are provided in a proportion such that x/y is a number equal to or greater than 1, z has a value greater than zero and $2x+3y-nz$ is a positive number and M, Q and E have such relative atomic sizes that the composition has a layered structure. Preferably, x/y is in the range of 1 to 12, more preferably x/y is in the range of 1 to 6, and most preferably is in the range of 1 to 4.

Divalent cations suitable for metal M broadly include elements selected from the Transition elements and Groups IIA, IVA and VA of the Periodic Table as well as certain rare earth elements. As specific examples can be mentioned magnesium, calcium, titanium, vanadium, chromium, manganese, iron, cobalt, nickel, palladium, platinum, copper, zinc, cadmium, mercury, tin and lead. Divalent metal cations which are particularly suitable are magnesium, nickel, cobalt, zinc, calcium, iron and copper. Suitable trivalent metal cations, Q, broadly include elements selected from the Transition elements and Groups IIIA and VA of the Periodic Table as well as certain rare earth elements and Actinide elements. As specific examples can be mentioned aluminum, antimony, titanium, scandium, bismuth, vanadium, yttrium, chromium, iron, manganese, cobalt, ruthenium, nickel, gold, gallium, thallium, and cerium. Trivalent metal cations which are particularly suitable can be selected from aluminum, iron and chromium.

The foregoing lists of suitable divalent and trivalent metal cations are meant to be illustrative not exclusive. Those skilled in the art will recognize that other cations can be used, provided that the specific type of the cations and their relative amounts (x/y ratio) result in a mixed metal framework composition of the desired layered structure in the presence of anion(s) E. Preferably, M is nickel, Q is aluminum, E is metavanadate and x/y is in the range of 1 to 6.

The compositions of formula (III) also can be calcined to prepare additional novel mixed metal framework compositions by heating at an elevated temperature for a suitable period of time. In some cases, the calcined compositions are more useful as catalysts for preparing alkylene glycols by liquid phase hydrolysis than the hydrated parent composition. Calcined compositions have the general formula:

$$M_x^{2+}Q_y^{3+}(O)_{(2x+3y-nz)/2}E_z^{n-} \quad (IV)$$

wherein the various symbols have the same meanings and values identified above in connection with formula (III). During the heat treatment, water and at least a portion of the volatile anions present in the hydrated composition, such as carbonates, are removed from the catalyst composition. The residue constitutes a mixed metal framework composition having a lattice of metal oxides. The calcining is conducted for a time and temperature to provide the desired properties.

As before, heat treating of these new mixed metal framework catalyst compositions can be done under an inert atmosphere, such as nitrogen or under an oxidizing atmosphere such as air. A suitable calcination temperature often is within the range of about 400° C. to 600° C. At this temperature a calcination period of about 12 to 24 hours often is suitable. Other calcination conditions can be identified using routine experimentation. It also is possible to heat treat the composition under a vacuum. In order to provide calcined compositions which can be hydrated back to a layered structure, generally the hydrated mixed metal framework catalyst composition normally should not be calcined above a temperature of about 600° C. At high temperatures, the layered structure of the originally hydrated composition is irreversibly altered. Temperatures within the range of about 400° to 500° C. have proved to be suitable for yielding calcined compositions that can be rehydrated to yield a layered structure.

Certain compositions falling within formula (I), such as hydrotalcite, which comprises a magnesium-aluminum hydroxide carbonate, and takovite, which comprises a nickel-aluminum hydroxide carbonate, are naturally occurring compositions. However, such compounds, as well as their related compositions, including the compositions of formula (III), also can be prepared synthetically from inexpensive starting materials using well-known coprecipitation techniques. Procedures for direct synthesis of such materials are described in Itaya et al., *Inorg. Chem.* (1987) 26:624–626; Taylor, R.M., *Clay Minerals* (1984) 19:591–603; Reichle, U.S. 4,476,324; Bish, D.L., *Bull. Mineral* (1980), 103:170–175 and Miyata et al., *Clays and Clay Minerals* (1977), 25:14–18, the disclosures of which are incorporated herein by reference. Using direct synthesis one has the ability to vary within wide limits the $M^{+2}/Q^{+3}$ atomic ratio as well as the anion.

For example, a composition of formula (I) or (III) where $M^{2+}$ is nickel or magnesium, $Q^{3+}$ is aluminum and $A^{n-}$ is metavanadate can be prepared by adding, as aqueous solutions, (a) a mixture of nitrates, sulfates or chlorides of nickel or magnesium and aluminum in a desired atomic ratio of nickel or magnesium to aluminum, e.g., 6 atoms of nickel as nickel chloride to 2 atoms of aluminum as aluminum chloride, to (b) an aqueous solution of a stoichiometric amount of sodium hydroxide and a water soluble salt of the desired anion, e.g., sodium metavanadate. The two solutions are mixed at a temperature of about 25° to 35° C. with vigorous stirring over a several-hour period to produce a slurry. The slurry then is heated for about 18 hours at a temperature within the range of about 50° to 200° C. (preferably between about 60° to 75° C.) in order to control crystallization and the ultimate particle size of the resulting crystals. After filtering, and thorough washing and drying, the solids are recovered, typically as a powder.

As noted above, this procedure can be adapted to a wide variety of cations, cation atomic ratios and anion substitutions. For example, water soluble salts of divalent magnesium, cobalt, zinc, copper, iron and calcium can be substituted for the nickel chloride illustrated above, while water soluble salts of trivalent iron and chromium can replace the aluminum chloride. A wide variety of other combinations also will be apparent to those skilled in the art. Generally, the rate of metal ion addition to the aqueous caustic/anion solution is not critical and can be varied widely. The reaction temperature also is not critical, although the temperature during the reaction preferably is kept below about 100° C. An important feature of the procedure is the use of efficient agitation during the mixing procedure to avoid the formation of undesired by-products.

Loading of an anion A, D or E into the mixed metal framework compositions of the present invention is influenced by a variety of factors including (i) the amount of anion used in the preparation relative to the metal cations, (ii) the atomic ratio of the metal cations (x/y) in the preparation procedure, (iii) the size of the cations and anions and (iv) the prepartion procedure. As used herein, "loading" is defined as the amount of available valencies provided by a desired anion A, D or E expressed as a percentage of the total available valencies for anion A, D or E. For example, vanadium loading in a takovite-type catalyst can be maximized by (1) using an excess (e.g., a greater than 3:1 molar ratio) of sodium metavanadate to aluminum chloride during catalyst preparation and (2) adjusting the atomic ratio of nickel to aluminum cations to about 2:1.

The crystallization step identified above also plays an important role in the preparation of the mixed metal framework compositions of the present invention. Absent this step, the product generally comprises a slurry containing essentially amorphous hydroxides. Thus, a suitable heat treating or crystallization period is important for producing solid catalytic material with a desired layered structure as characterized by a well-defined X-ray diffraction pattern. Generally, the higher the crystallization temperature and the longer the heating time, the larger is the particle size of the resulting crystals. If the crystallization temperature is too low (typically less than about 50° C.), the rate of crystal formation may be too slow to be commercially practical. On the other hand, elevated temperatures promote too rapid a crystal growth and may yield crystal particles larger than desired.

Mixed metal framework compositions suitable as catalysts also can be prepared from the native or synthetic hydrotalcite-type compositions by ion exchange. For example, hydrotalcite can be treated at ambient conditions with 0.01N phosphoric acid for about 18 hours to replace the carbonate anion with phosphate anion. A halide analog of hydrotalcite prepared directly or by anion-exchange could be contacted with molybdic acid or a water soluble salt thereof, or with a water soluble salt of tungstic acid or vanadic acid in order to substitute the transition metal anion for the halide anion in the catalyst structure thereby to produce a mixed metal framework composition of formula (I) or (III). Other ion exchanges will be apparent to those skilled in the art.

Reversibly calcined hydrotalcite-type materials also can be neutralized using an acid of the desired anion in order to produce suitable catalysts. For example, a mixed metal framework composition wherein the desired anion is molybdate can be formed by neutralizing a highly alkaline form of a hydrotalcite-type composition with molybdic acid. Such alkaline hydrotalcite-type compositions can be prepared by calcination of the hydrated material. Direct synthetic preparative procedures such as coprecipitation generally are preferred for making the mixed metal framework composition.

The powdered mixed metal framework composition can be used for heterogeneous catalysis as is or can be pelleted or extruded with or without added binder in order to form larger particles more suitable for use in fixed bed reactors, fluid bed reactors, slurry reactors and the like. Some catalyst compositions, for example, compositions where the anion is molybdate or vanadate, can be formed into pellets having a sufficient structural integrity for some purposes without adding any significant level of binder. In order to form useful pellets with other catalyst compositions, however, such as those having tungstate as the anion, a binder generally is required. Compositions also may be supported on a suitable carrier. As will be appreciated by those skilled in the art, the use of a binder may be desired in certain applications, regardless of the anion.

The catalytic hydrolysis of alkylene oxide using the broad class of heterogeneous mixed metal framework catalyst compositions of the present invention identified above can be conducted in either the liquid or vapor phase. However, as explained, certain compositions are more suited to either a liquid phase or vapor phase process. In fact, some compositions exhibit better catalytic activity and selectivity in one process as compared to that in the other.

In accordance with the present invention, a mixture of alkylene oxide and water, in either the liquid or vapor state is contacted with a suitable mixed metal framework composition to catalyze the hydrolysis of the alkylene oxide selectively to the monoalkylene glycol.

In the case of a liquid phase hydrolysis reaction, the process usually is carried out at a temperature between about 20° C. and 250° C., preferably between about 50° C. and 200° C. While the process may be conducted at a variety of pressures, the reaction conveniently is conducted at pressures greater than atmospheric, for example, between about 25 psig and 10,000 psig and preferably between about 25 psig and 1500 psig. Of course, the reaction temperature and pressure need to be selected to maintain liquid reaction conditions. The pH of the liquid reaction system also can affect both the rate and selectivity of the reactions leading to the desired monoalkylene glycol product. In general, the pH of the liquid reaction system is between about 3 and 13, preferably between about 6 and 9.

In the conventional liquid phase hydrolysis system, ethylene oxide first is recovered from the outlet stream of the ethylene oxide reactors by scrubbing and stripping with water. The enriched ethylene oxide stream then is purified and hydrolyzed to glycol. Water in the effluent from the hydrolysis is removed in a series of multi-effect evaporators. In addition to their capital costs, both the ethylene oxide recovery/refining system and the evaporation train are very energy intensive.

In a vapor phase process, significant economy of operation is possible by conducting the vapor phase hydrolysis at the alkylene oxide reactor outlet and eliminating the alkylene oxide refining system and the evaporation train. A vapor phase hydrolysis process typically is operated at a higher temperature sufficient under the conditions of pressure and composition to maintain the fluid in the vapor phase during the reaction. Often the temperature is in the range of about 160° C. to 290° C., preferably about 180° C. to 260° C. Reaction pressures from subatmospheric to 750 psig are suitable, while a pressure between 150 psig and 300 psig is preferred. Of course, conditions must be selected which maintain the reactants in the vapor state. Because of flammability limits, the feed gas normally contains less than about 11 percent alkylene oxide (by weight). A gas hourly space velocity for the vapor phase process may range between about 1000 hr$^{-1}$ to 16,000 hr$^{-1}$, with a value between 2000 hr$^{-1}$ to 6000 hr$^{-1}$ generally being preferred.

Vicinal alkylene oxides suitable for preparing monoalkylene glycols using the catalytic procedures of the present invention have the formula

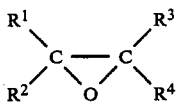

wherein $R^1$, $R^2$, $R^3$ and $R^4$ each designate a hydrogen atom, an alkyl group having between 1 and about 10 carbon atoms (preferably between 1 and 4 carbon atoms), an aryl group having at least 6 carbon atoms, (for example, a monocyclic or bicyclic aryl), an alkenyl group having 2 or 3 carbon atoms or a cycloalkyl group having 3 to 6 carbon atoms, and $R^1$ and $R^3$ may be joined to form a cyclic structure. Representative of the alkylene oxides which may be used in the present invention are ethylene oxide, propylene oxide, butylene oxide (including isobutylene oxide, 1,2-butylene oxide and 2,3-butylene oxide), pentylene oxide, cyclohexene oxide, styrene oxide and the like. Preferably, the alkylene oxide is an aliphatic alkylene oxide such as ethylene oxide and propylene oxide. Ethylene oxide is particularly preferred. The present invention will be described primarily with reference to ethylene oxide.

Generally, the source of the alkylene oxide is not important. Of course, impurities which may interfere with the formation of the desired monoalkylene glycol or deactivate the mixed metal framework catalyst composition should be removed. Ethylene oxide produced by the catalytic oxidation of ethylene with molecular oxygen or an oxygen-containing gas in the presence of a silver catalyst typically is recovered at a high purity and can be suitably employed without any pretreatment.

Water of a sufficient purity to provide the desired quality alkylene glycol product also should be used. Normally, in the liquid phase process, between about 1 and about 40 moles of water are used per mole of alkylene oxide. To reduce energy and equipment costs, the molar hydrolysis ratio typically is adjusted to a value between about 1 and 25. A slight molar excess of water over the stoichiometric amount required generally is desired to maintain high selectivity in the conversion of alkylene oxide to the desired monoalkylene glycol product. In a vapor phase process, the molar hydrolysis ratio is between about 1 and the ratio prevailing at the water vapor saturation pressure under the reaction conditions. Generally, conditions are selected to provide a molar hydrolysis ratio between about 1 and 10, preferably between about 1 and 5.

In either the liquid or vapor phase process the reaction can be carried out in the presence of a diluent gas such as air, argon, nitrogen, methane and the like. Carbon dioxide also may be present during the hydrolysis of the alkylene oxide. In many cases an amount of carbon dioxide up to about 15 molar percent may be inherent when the alkylene oxide is produced by epoxidation of an alkene. When present, e.g., in an amount of up to about 6 molar percent, carbon dioxide also may enhance the selectivity provided by certain catalyst compositions of the present invention particularly in connection with vapor phase hydrolysis as described below in more detail.

The mass flow of the reactants over the mixed metal framework catalyst composition generally is adjusted so as to provide the desired rate enhancement and selectivity. Preferably, the reaction is conducted for a sufficient period of time to ensure maximum conversion of alkylene oxide. The time needed for maximum conversion is a function of a variety of parameters including temperature, level of reactants, and the like, and is within the skill of the art.

The process of the invention can be carried out either as a batch reaction or as a continuous process, with recycle of unconsumed reactants if required. For commercial glycol products, a continuous process is preferred.

Alkylene glycol may be recovered from the reactor effluent in any convenient manner and procedures are known to those skilled in the art, e.g., by distillation or condensation. An important feature of the present invention is the use of a hydrothermally stable, solid catalyst composition which is readily separated from the hydrolysis product stream. In the context of the present invention, the phrase "hydrothermally stable" means that the mixed metal framework catalyst compositions of the present invention remain active at the elevated temperature conditions of liquid and vapor phase alkylene oxide hydrolysis without experiencing an excess loss of catalyst constituents, e.g., by leaching. Typically, when a liquid phase process is used to prepare alkylene glycol, the water recovered with the product glycol is removed in a series of multiple-effect evaporators and the alkylene glycol is further refined by vacuum distillation. One advantage of the vapor phase process is that recovery of alkylene glycol is facilitated significantly since it can be recovered by condensation. Purification of the glycol product can be effected by any convenient means such as by distillation.

Vanadate is a preferred anion for a liquid phase, mixed metal framework, alkylene oxide hydrolysis catalyst composition of the present invention. Tests have shown that vanadate-containing catalysts provide a significant degree of selectivity enhancement to monoethylene glycol. Furthermore, since magnesium showed a higher tendency to leach from hydrotalcite-type catalyst compositions than nickel did from the takovite family of catalyst compositions, vanadate-containing takovite catalysts are preferred relative to vanadate-containing hydrotalcites.

Commercial rates of monoethylene glycol production can be obtained in the liquid phase process using either the uncalcined or calcined mixed metal framework catalyst compositions of the present invention. Calcined compositions frequently exhibit a higher level of selectivity than uncalcined compositions, especially in the liquid hydrolysis process. Importantly, if a calcined mixed metal framework catalyst composition of the present invention experiences any decline in selectivity, it can be regenerated by a heat treatment to restore at least a portion of its initial level of selectivity enhancement and reused. Conditions discussed above for calcining the hydrated mixed metal oxide compositions of the present invention are suitable for regenerating compositions which have experienced a decline in activity.

Catalysts having the formulas (I) and (II) above wherein M is at least one of magnesium, nickel, cobalt, zinc and copper, Q is aluminum, A is at least one of carbonate, bicarbonate, phosphate, sulfate, vanadate, tungstate and molybdate, x/y is between 1 and 12, z has a value which satisfies the relationship: x/z is between n and 12n, and a is a positive number, are generally preferred for vapor phase hydrolysis of alkylene oxide due to their combination of activity (conversion of alkylene oxide) and selectivity.

Higher selectivity for the monoalkylene glycol is particularly important for heterogeneous vapor phase alkylene oxide hydrolysis catalysts. Polyglycols which tend to be formed with catalysts of lower selectivities may accumulate on the catalyst surface. Such accumulation generally leads to still lower selectivity and catalyst deactivation. Best results have been obtained in a vapor phase process using a hydrotalcite catalyst wherein $M^{2+}$ is magnesium, $Q^{3+}$ is aluminum, $A^{n-}$ is carbonate, x/y is about 3, and z is about 1, in the presence of up to 3% added carbon dioxide. When this preferred hydrotalcite catalyst is used without added carbon dioxide, the catalyst experiences some carbonate decomposition which tends to reduce selectivity. Levels of added carbon dioxide higher than about 3% may tend in some instances to inhibit the hydrolysis reaction leading to lower conversion.

The compositions of this invention also may find application as catalysts, for example, for oxidation or organic material processing, as binders and matrix materials in fabricating catalysts, adsorbents, ion-exchangers and the like, especially for high temperature operations, and in dielectric composition components.

The following examples are provided to assist in the understanding of the invention and are not intended to be limitations on the scope of the disclosure. All reported percentages and parts of solid are by weight and all reported percentages and parts of liquids and gases are by volume, unless otherwise specifically indicated.

EXAMPLE 1

Preparation of Ni-Al-VO₃ Takovite Catalyst

A 1.0 liter flask, equipped with an addition funnel, mechanical stirrer, reflux condenser and thermometer, was purged with nitrogen and filled with 300 milliliters of a solution containing 42.0 grams of sodium hydroxide and 36.6 grams of sodium metavanadate. To this was added, slowly over a 0.5 hour period with good agitation, 210 milliliters of a solution containing 71.3 grams of nickel chloride hexahydrate and 23.9 grams of aluminum chloride hexahydrate. A slight exotherm occurred and a bluish green precipitate immediately appeared. The temperature of the suspension was held at 65° C. with constant stirring overnight to obtain the desired particle size. The slurry was cooled and filtered and the solids were washed and dried.

EXAMPLES 2 TO 8

Several compounds having a hydrotalcite-type (magnesium/aluminum) or takovite-type (nickel/aluminum) molecular formula were directly synthesized using the procedure of Example 1, by replacing the sodium metavanadate of Example 1 with a water soluble salt having the desired anion. In Examples 3–4 and 5–6 sodium molybdate and sodium tungstate, respectively, were used as the anion-containing salt. Also, the water soluble nitrate salts were used in place of the chloride in preparing the hydrotalcite and takovite catalysts of Examples 7 and 8. The resulting catalysts (including catalyst 1 from Example 1) are identified below in Table 1. As noted, the loading of the desired anion into the catalyst composition was not complete. Apparently, carbonate anions formed from atmospheric carbon dioxide, either during the reaction or during the work-up of the product, also were incorporated into the inorganic structure.

TABLE 1

HYDROTALCITE AND TAKOVITE CATALYSTS PREPARED BY DIRECT SYNTHESIS

| Catalyst Example No. | Molecular Formula | Transition Metal Anion Loading (%) |
|---|---|---|
| 1 | $Ni_{6.3}Al_2(OH)_{15.8}(CO_3)_{0.7}(VO_3)_{1.5}\cdot 6\ H_2O$ | 52 |
| 2 | $Mg_{7.1}Al_2(OH)_{17.9}(CO_3)_{0.8}(VO_3)_{0.7}\cdot 6\ H_2O$ | 30 |
| 3 | $Ni_{6.3}Al_2(OH)_{15.2}(CO_3)_{1.4}(MoO_4)_{0.3}\cdot 8\ H_2O$ | 18 |
| 4 | $Mg_{5.6}Al_2(OH)_{16.2}(CO_3)_{0.4}(MoO_4)_{0.1}\cdot 7\ H_2O$ | 20 |
| 5 | $Ni_{6.26}Al_2(OH)_{15.6}(CO_3)_{1.44}(WO_4)_{0.03}\cdot 13\ H_2O$ | 2 |
| 6 | $Mg_{8.1}Al_2(OH)_{20.8}(CO_3)_{0.6}(WO_4)_{0.1}\cdot 10\ H_2O$ | 14 |
| 7 | $Ni_{6.14}Al_2(OH)_{14.74}(CO_3)_{1.77}\cdot 7\ H_2O$ | — |
| 8 | $Mg_6Al_2(OH)_{16}(CO_3)\cdot 4\ H_2O$ | — |

EXAMPLE 9

A catalyst having the following molecular formula:

$$Mg_{6.65}Al_2(OH)_{14.77}(CO_3)_{1.87}(MoO_4)_{0.79}\cdot H_2O$$

was prepared by neutralizing 10 grams of calcined hydrotalcite with 5.5 liters of 0.01N molybdic acid. The neutralization suspension was stirred vigorously at room temperature for 18 hours under a nitrogen atmosphere. The solid recovered by filtration was dried overnight in a vacuum oven at 125° C. On the basis of elemental analysis and X-ray diffraction, the product was identified as a hydrotalcite and was assigned the above structure.

EXAMPLE 10

Using the preparation procedure of Example 1, the effect of increasing the amount of sodium metavanadate during catalyst preparation on the resulting vanadate loading in the catalyst was examined. At a molar ratio of sodium metavanadate to aluminum chloride of 1.5:1, a vanadate loading of about 36% was attained. Increasing this molar ratio to 3.0:1 more than doubled the loading to about 81%.

EXAMPLE 11

Again using the catalyst preparation procedure of Example 1, compositions containing varying nickel to aluminum atomic rations were prepared. A constant molar ratio of sodium metavanadate to aluminum chloride of 1.5 was used throughout the test work. The results are shown below in Table 2.

TABLE 2
EFFECT OF Ni/Al RATIO ON VANADATE LOADING

| Catalyst No. | Ni/Al Mole Ratio | Molecular Formula | Vanadium Loading* (%) |
|---|---|---|---|
| 11A | 4.02 | $Ni_{8.03}Al_2(OH)_{18.17}(CO_3)_{1.24}(VO_3)_{1.38}\cdot 6H_2O$ | 35.75 |
| 11B | 3.15 | $Ni_{6.33}Al_2(OH)_{15.8}(CO_3)_{0.7}(VO_3)_{1.5}\cdot 6H_2O$ | 52.00 |
| 11C | 2.19 | $Ni_{4.38}Al_2(OH)_{13.21}(CO_3)_{0.33}(VO_3)_{0.89}\cdot 4H_2O$ | 57.42 |
| 11D | 1.44 | $Ni_{2.88}Al_2(OH)_{10.31}(CO_3)_{0.37}(VO_3)_{0.71}\cdot 3H_2O$ | 48.97 |

*calculated as $VO_3$

EXAMPLE 12

In order to determine what effect calcination has on the hydrated mixed metal framework catalyst compositions of the present invention, several catalysts were heat treated at 450° C. under a nitrogen atmosphere for 18 hours. Included were catalysts 11A, 11C and 11D from Example 11. The catalysts were characterized by elemental analysis, X-ray diffraction and infrared spectroscopy. The structure (molecular formula) and vanadate level are detailed below in Table 3. Calcination did not affect the molar amount of vanadium relative to aluminum that existed in the uncalcined hydrated material.

TABLE 3
CALCINED VANADATE/TAKOVITE CATALYSTS

| Catalyst Number | Molecular Formula | Vanadium Loading* (wt %) |
|---|---|---|
| 12A | $Ni_{8.03}Al_2O_{10.33}(VO_3)_{1.38}$ | 16.51 |
| 12C | $Ni_{4.38}Al_2O_{6.93}(VO_3)_{0.89}$ | 17.27 |
| 12D | $Ni_{2.88}Al_2O_{5.53}(VO_3)_{0.71}$ | 18.40 |

*calculated as $VO_3$

EXAMPLE 13

Both the uncalcined hydrated catalyst compositions of Example 11 and the corresponding calcined catalyst compositions of Example 12 were tested for their influence on the liquid phase hydrolysis of ethylene oxide at a temperature of about 160° C. and a pressure of about 200 psig using a weight ratio of water to ethylene oxide of about 9.0 (molar hydrolysis ratio of about 22). The performance results at the end of a one-day test are presented below in Table 4. In all cases, the ethylene oxide conversion was essentially complete and the monoethylene glycol selectivity was enhanced relative to the uncatalyzed ethylene oxide hydrolysis.

TABLE 4
CATALYZED EO HYDROLYSIS EXPERIMENTS SUMMARY OF ONE-DAY RESULTS

| Catalyst Example No. | T (°C.) | P (psig) | t (hr.) | Molar Hydrolysis Ratio | Monoethylene Glycol Selectivity (%) |
|---|---|---|---|---|---|
| UN-CALCINED | | | | | |
| 11A | 161 | 197 | 28 | 9.1 | 93.5 |
| 11C | 160 | 197 | 24 | 8.6 | 94.2 |
| 11D | 159 | 198 | 27 | 9.4 | 94.1 |
| CALCINED | | | | | |
| 12A | 166 | 198 | 25 | 10.6 | 95.7 |
| 12C | 160 | 199 | 27 | 9.0 | 93.7 |
| 12D | 160 | 198 | 25 | 9.2 | 95.0 |

EXAMPLE 14

Catalysts of the following compositions were prepared using the procedure of Example 1:

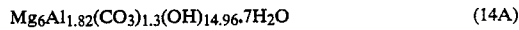

$Mg_6Al_{1.82}(CO_3)_{1.3}(OH)_{14.96}\cdot 7H_2O$     (14A)

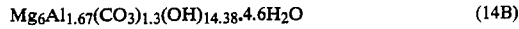

$Mg_6Al_{1.67}(CO_3)_{1.3}(OH)_{14.38}\cdot 4.6H_2O$     (14B)

and were tested for their activity and selectivity in hydrolyzing ethylene oxide to monoethylene glycol in the vapor phase. The analytically determined carbonate loadings for catalysts (14A) and (14B) actually are higher than the theoretical limit of 1.0 suggesting that some of the carbon is present either as absorbed carbon dioxide or as bicarbonate. The catalysts were tested at a temperature of 200° C., a pressure of 150 psig, a molar hydrolysis ratio of about 2.4 and a gas hourly space velocity of 5300 reciprocal hours using a feed stream containing about 2 percent ethylene oxide and different carbon dioxide levels. The test results are reported below in Table 5. As shown, ethylene oxide conversions varied between 52–100 percent with selectivities in the range of 60 to 87%.

TABLE 5
RESULTS OF $CO_2$ EXPERIMENTS

| Catalyst | $CO_2$ Concentration Vol. % | EO Conversion (%) | Monoethylene Glycol Selectivity (%) |
|---|---|---|---|
| 14A | 0.0 | 100 | 60 |
| 14B | 3.0 | 86 | 89 |
| 14B | 3.0 | 52 | 82 |
| 14B | 0.4 | 84 | 84 |
| 14B | 0.0 | 98 | 65 |
| 14B | 1.0 | 86 | 82 |
| 14B | 1.0 | 82 | 83 |
| 14B | 3.5 | 68 | 87 |

EXAMPLE 15

A hydrotalcite-type material of the takovite family was synthesized by first preparing a solution of 29.1 gm of nickel nitrate hexahydrate and 12.5 gm of aluminum nitrate nonahydrate in 70 ml of distilled water. A separate solution of 24 gm of sodium hydroxide and 10 g of sodium carbonate in 100 ml of distilled water was prepared in a 500 ml round-bottomed reaction flask fitted with a mechanical stirrer, a thermometer and condenser. With good stirring, the nitrate solution was added dropwise to the solution in the reaction flask over a 20 minute period at room temperature. The resulting slurry was heated to 65° C. and stirred overnight. 13.7 gm of a green precipitate was recovered by filtering, thorough washing, and drying. X-ray and IR analyses identified the material as a hydrated mixed metal framework composition of the takovite family. This composition can be used for the catalysis of alkylene oxide hydrolysis.

Although certain embodiments of the invention have been described in detail, it will be appreciated that other embodiments are contemplated along with modifications of the disclosed features, as being within the scope of the invention, which is defined in the appended claims.

We claim:

1. A process for producing monoalkylene glycol which comprises reacting a vicinal alkylene oxide with water as either a liquid or vapor in the presence of a hydrothermally stable mixed metal framework catalyst composition selected from at least one of (a) a material having the stoichiometric formula:

$$M_x^{2+}Q_y^{3+}(OH)_{2x+3y-nz}A_z^{n-}\cdot a\,H_2O \qquad (I)$$

wherein M is at least one divalent metal cation; Q is at least one trivalent metal cation; and A is at least one anion providing a valence $(n-)$, wherein n is 1 to 4 and wherein a is a positive number, M, Q, and A are provided in a proportion such that x/y is a number equal to or greater than 1, z has a value greater than zero and $2x+3y-nz$ is a positive number, and M, Q and A are selected to provide a layered structure, and (b) a material prepared by calcining the material of stoichiometric formula (I) having the formula $$M_x^{2+}Q_y^{3+}(O)_{(2x+3y-nz)/2}D_z^{n-} \qquad (II)$$

wherein M, Q, x, y, z and n have the same meanings defined above in connection with formula (I), and D is at least one nonvolatile anion.

2. The process of claim 1 wherein x/y is a number between 1 and 12 and z has a value which satisfies the relationship: x/z is between n and 12n.

3. The process of claim 2 where A is selected from the group consisting of carbonate, halide, cyanide, phosphite, phosphate, chromate, sulfate, oxalate, acetate, nitrate, hexanoate, sebacate, vanadate, molybdate, tungstate and ferrocyanate.

4. The process of claim 1 wherein D is selected from the group consisting of halides, phosphite, phosphate, vanadate, molybdate, tungstate, sulfite, sulfate, chromate, arsenate, borate, and chlorate.

5. The process of claim 1 wherein x/y is a number between 1 and 6 and z has a value which satisfies the relationship: x/z is between n and 6n.

6. The process of claim 2 wherein said material prepared by calcining the material of formula (I) has been heat treated at a temperature in the range of 400° C. to 600° C. for 12 to 24 hours.

7. The process of claim 5 wherein M is selected from magnesium and nickel and Q is aluminum.

8. The process of claim 1 wherein said vicinal alkylene oxide and water are reacted in the liquid phase in the presence of a hydrothermally stable mixed metal framework catalyst composition selected from at least one of (a) a material having the stoichiometric formula $$M_x^{2+}Q_y^{3+}(OH)_{2x+3y-nz}A_z^{n-}\cdot a\,H_2O \qquad (IA)$$

wherein M is at least one member selected from magnesium, nickel, iron, cobalt, zinc, calcium and copper; Q is at least one member selected from aluminum, iron and chromium; A is at least one anion selected from vanadate, molybdate and tungstate and wherein a is a positive number, x/y is a number between 1 and 12, z has a value which satisfies the relationship, x/z is between n and 12n and M, Q and A are selected to provide a layered structure, and (b) a material prepared by calcining the material of formula (IA) having the stoichiometric formula $$M_x^{2+}Q_y^{3+}(O)_{(2x+3y-nz)/2}D_z^{n-} \qquad (IIA)$$

wherein M, Q, x, y, n and z have the same meanings defined above in formula (IA) and D is equivalent to A.

9. The process of claim 8 wherein x/y is a number between 1 and 6 and z has a value which satisfies the relationship: x/z is between n and 6n.

10. The process of claim 8 wherein said material prepared by calcining the material of formula (IA) has been heat treated at a temperature in the range of 400° C. to 600° C. for 12 to 24 hours.

11. The process of claim 9 wherein M is selected from magnesium and nickel and Q is aluminum.

12. The process of claim 1 wherein said vicinal alkylene oxide and water are reacted in the vapor phase in the presence of a hydrothermally stable, mixed metal framework catalyst composition selected from at least one (a) a material having the stoichiometric formula $$M_x^{2+}Al_y^{3+}(OH)_{2x+3y-nz}A_z^{n-}\cdot a\,H_2O \qquad (IB)$$

wherein M is at least one member selected from magnesium, nickel, cobalt, zinc and copper, A is at least one member selected from carbonate, bicarbonate phosphate, vanadate, tungstate and molybdate, x/y is between 1 and 12, z satisfies the relationship, x/y is between n and 12n and a is a positive number, and (b) a material prepared by calcining the material of formula (IB) having the stoichiometric formula $$M_x^{2+}Al_y^{3+}(O)_{(2x+3y-nz)/2}D_z^{n-} \qquad (IIB)$$

wherein M, x, y, z and n have the same meanings defined above in connection with formula (IB) and D is at least one nonvolatile anion selected from phosphate, vanadate, tungstate and molybdate.

13. The process of claim 12 wherein x/y is a number between 1 and 6 and z has a value which satisfies the relationship: x/y is between n and 6n.

14. The process of claim 13 wherein said material prepared by calcining the material of formula (IB) has been heat treated at a temperature in the range of 400° C. to 600° C. for 12 to 24 hours.

15. The process of claim 14 wherein M comprises magnesium, A comprises carbonate and at least one nonvolatile anion and x/y is in the range of 1 to 3.

16. The process of claim 15 wherein said alkylene oxide and water are reacted in the presence of up to 3% by volume added carbon dioxide.

* * * * *